United States Patent [19]
Tsuchiya et al.

[11] Patent Number: 4,857,238
[45] Date of Patent: Aug. 15, 1989

[54] MANUFACTURING METHOD FOR ALKYLDIHALOGENOPHOSPHINES

[75] Inventors: Hiromu Tsuchiya; Shukichi Nabekawa; Masao Takada, all of Tokyo, Japan

[73] Assignee: Nippon Chemical Industrial Co., Ltd., Tokyo, Japan

[21] Appl. No.: 225,169

[22] Filed: Jul. 28, 1988

[30] Foreign Application Priority Data

Apr. 28, 1988 [JP] Japan ................................ 63-103794

[51] Int. Cl.$^4$ ............................................... C07F 9/52
[52] U.S. Cl. .................................................. 562/820
[58] Field of Search ................................... 260/543 P

[56] References Cited

U.S. PATENT DOCUMENTS

| | | | |
|---|---|---|---|
| 2,875,224 | 2/1959 | Van Winkle et al. | 260/543 P |
| 3,029,282 | 4/1962 | Toy et al. | 260/543 P |
| 3,078,304 | 2/1963 | Niebergall et al. | 260/543 P |
| 3,149,144 | 9/1964 | Huffman | 260/543 P |
| 3,259,671 | 7/1966 | Jungermann | 260/543 P |
| 3,458,569 | 7/1969 | Mellon | 260/543 P |
| 3,557,204 | 1/1971 | Weinberg | 260/543 P |
| 3,584,043 | 6/1971 | Maier | 260/543 P |
| 3,751,460 | 8/1973 | Schliebs | 260/543 P |
| 3,813,435 | 5/1974 | Wood | 260/543 P |
| 3,829,479 | 8/1974 | Kent | 260/543 P |
| 3,840,576 | 10/1974 | Coates et al. | 260/543 P |
| 4,155,932 | 5/1979 | Masaki et al. | 260/543 P |
| 4,521,346 | 6/1985 | Kleiner | 260/543 P |
| 4,536,351 | 8/1985 | Neumaier | 260/543 P |

FOREIGN PATENT DOCUMENTS

| | | |
|---|---|---|
| 1119861 | 9/1959 | Fed. Rep. of Germany . |
| 1119862 | 9/1959 | Fed. Rep. of Germany . |
| 1139491 | 12/1959 | Fed. Rep. of Germany . |
| 3340995 | 5/1985 | Fed. Rep. of Germany . |
| 173764 | 7/1964 | U.S.S.R. . |
| 539039 | 12/1976 | U.S.S.R. . |

Primary Examiner—Paul J. Killos
Attorney, Agent, or Firm—Oblon, Spivak, McClelland, Maier & Neustadt

[57] ABSTRACT

A manufacturing method for an alkyldihalogenophosphine uses an alkyl halide and a trihalide of phosphorus as starting materials. A reaction product which is formed by an FC reaction is reduced by yellow phosphorus in the presence of iodine, whereby an alkyldihalogenophosphine is manufactured. A high-purity alkyldihalogenophosphine can be manufactured with a high yield by using an excess amount of a trihalide of phosphorus, which can act as a reaction solvent.

8 Claims, No Drawings

MANUFACTURING METHOD FOR ALKYLDIHALOGENOPHOSPHINES

BACKGROUND OF THE INVENTION

This invention relates to an industrial manufacturing method for alklydihalogenophosphines, which are industrially useful as intermediates in the manufacture of pesticides, flame retardants, and other organic phosphorus compounds.

Alkyldihalogenophosphines, and particularly the industrially useful compound methyldichlorophosphine, can be manufactured by the direct reaction of phosphorus trichloride and methane in the presence of carbon tetrachloride at a temperature of at least 500° C. Manufacturing methods employing direct reaction are disclosed in Japanese Published Unexamined Pat. applications Nos. 53-5123, 53-18517, 53-23929, and 58-116494.

On the other hand, the Friedel-Crafts reaction between alkylchlorides and phosphorus trichloride is well known. Alkyldichlorophosphines can be manufactured by reacting the complex which is formed by the Friedel-Crafts reaction using red phosphorus, antimony, or the like as a reducing agent. See Zhur. Obshch. Khim (Vol. 28, pp. 2963–2965 (1958)) or Canadian Journal of Chemistry (Vol. 41, p. 2299 (1963)).

The above-described manufacturing method for methyldichlorophosphine in which phosphorus trichloride and methane are directly reacted is important because it is an extremely rational method, but since it is a vapor phase reaction carried out at a high temperature of at least 500° C., the materials forming the reaction apparatus must be carefully selected, and as the raw materials are chlorides, special precautions must be taken to prevent environmental pollution. In addition, not only is the reaction dangerous, but it produces many by-products, and the separation of the desired product from the by-products is extremely difficult.

On the other hand, the method in which the complex which is formed as the reaction product of the Friedel-Crafts reaction between alkylchloride and phosphorus trichloride is then reduced is a solid-solid, solid-liquid or liquid-liquid reaction, so treatment is easy compared to the treatment required for the direct reaction method. However, even if the complex which is formed as a reaction product is reduced with a reducing agent such as red phosphorus, subsequent processes are necessary to obtain the desired product. In the subsequent processes, a large amount of aluminum chloride (AlCl₃) is formed, and the separation and treatment thereof are difficult, so it is difficult to recover high-purity alkyldichlorophosphine with a high yield. For example, if red phosphorus is used as a reducing agent, as the reaction is carried out at a high temperature without a solvent, it is difficult to perform the reaction industrially. If antimony is used as a reducing agent, the inclusion of impurities is unavoidable.

There is also a method in which the complex (Cl₃C-PCl₃·AlCl₄) which is formed as a reaction product of the Friedel-Crafts reaction is reduced using yellow phosphorus as a reducing agent (U.S. Pat. No. 2875224). However, not only is the reaction inadequate, but that patent does not teach a manufacturing method for alkyldihalogenophosphines.

SUMMARY OF THE INVENTION

In light of the above circumstances, the present inventors performed extensive research with the aim of obtaining an industrially advantageous manufacturing method for alkyldihalogenophosphines. It was found that if the Friedel-Crafts reaction is carried out in the presence of an excess amount of a trihalide of phosphorus, if the complex which is formed by the Friedel-Crafts reaction is reduced in the presence of iodine using yellow phosphorus as a reducing agent, the reaction progresses effectively.

Accordingly, the present invention is a manufacturing method for alkyldihalogenophosphines in which the reaction product of the Friedel-Crafts reaction between an alkyl halide and a trihalide of phosphorus is reduced to form alkyldihalogenophosphine, characterized in that excess amount of a trihalide of phosphorus, which can act as a reaction solvent, is employed.

DESCRIPTION OF THE PREFERRED EMBODIMENTS

Hereinbelow, the manufacturing method of the present invention will be described in further detail. As stated above, the Friedel-Crafts reaction (hereinunder referred to the FC reaction) is carried out between an alkyl halide and a trihalide of phosphorus.

Typical examples of an alkyl halide which can be used as a starting material are methyl chloride (CH₃Cl) and ethyl chloride (C₂H₅Cl). Preferably, methyl chloride is employed.

Some examples of a trihalide of phosphorus are phosphorus trichloride (PCl₃) and phosphorus tribromide (PBr₃), with phosphorus trichloride being preferable.

Other raw materials of course include anhydrous aluminum chloride (AlCl₃), which is a catalyst for the FC reaction. One of the advantageous characteristics of the present invention is that during the FC reaction, an excess amount of a phosphorous trihalide, which can function as a reaction solvent, is employed.

The suitable amount of phosphorus chloride is connected with the amount of the below-mentioned alkyl halide which is added. It should be used in an amount of 4–10 moles and preferably 5–6 moles for every one mole of anhydrous aluminum chloride, which serves as a catalysts for the FC reaction. If phosphorus chloride is used in an amount of less than about 4 moles, the solid complex which is formed as a reaction product does not crystallize as crystallites but tends to become a massive solid which adheres to the walls of the reaction vessel, making subsequent operations difficult. Another solvent which can be used optionally is methylene chloride (CH₂Cl₂). At high temperatures, methylene chloride brings about the FC reaction. Therefore, at high temperatures, it can be used together with the above-mentioned alkyl halide as a starting material.

As mentioned earlier, the fundamental mechanism of the FC reaction using the above-mentioned starting materials is well know. When methyl chloride and phosphorus trichloride are employed, the FC reaction is a two-stage exothermic reaction expressed by the following equations I and II.

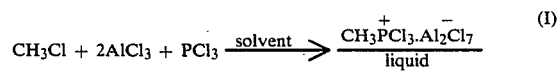
(I)

-continued $$CH_3Cl + \overset{+}{CH_3PCl_3}.\overset{-}{Al_2Cl_2} + PCl_3 \xrightarrow{\text{solvent}} \underset{\text{solid}}{2\overset{+}{CH_3PCl_3}.\overset{-}{AlCl_4}} \quad (II)$$

The complex which is formed as a reaction product in the reaction stage of Equation I is a liquid, and the complex which is the final reaction product of the reaction stage of Equation II is a solid.

This FC reaction is carried out using a desired solvent. In the present invention, anhydrous aluminum chloride and a trihalide of phosphorus in an amount sufficiently large that the excess trihalide of phosphorus can act as a solvent are charged into a pressure-resistant vessel, and an alkyl halide such as methyl chloride is added in a controlled manner, whereby a high yield can be obtained.

Namely, in the FC reaction which progresses in two stages as described above, the reaction stage described by Equation I, proceeds relatively fast. Therefore, the length of time over which addition is performed need only be long enough to prevent the sudden generation of heat of reaction.

On the other hand, in the second stage of the reaction, it is necessary to add the alkyl halide as slowly as possible. This is because, as stated earlier, the solid complex must crystallize as crystallites, and whether crystallization takes place or not determines the stability of the subsequent operations and directly influences the yield of the resulting dihalogenophosphine.

Accordingly, during the reaction given by Equation I, the alkyl halide should be added over a period of 1–3 hours, and during the reaction given by Equation II, it should be added over a period of at least 3 hours and preferably of 6–8 hours.

This FC reaction is carried out under pressure with the temperature controlled so as to be 50–70° C. After the addition of the alkyl halide, the temperature is maintained at 80° C. or above, and preferably at 85–95° C. for several hours to perform aging and make the reaction go to completion, whereby a crystallite complex is obtained.

Next, the FC reaction product which is obtained in the above manner is reduced by yellow phosphorus in the presence of iodine ($I_2$) in an amount sufficient for it to act as a catalyst. This is an important characteristic of the present invention.

In this case, directly carrying out the reduction reaction in the system of the complex which is fored as the FC reaction product is within the scope of the present invention. However, the system of the reaction product is a slurry containing crystalline grains of the reaction product. Therefore, in order to carry out reduction effectively, it is desirable to transfer the slurry to a separate reaction vessel, completely dissolve it in a solvent, and carry out the reaction in a liquid phase system.

For this purpose, an organic solvent having affinity for aluminum chloride is used, some examples of which are a diester of phthalic acid such as dimethyl phthalate, diethyl phthalate, or dibutyl phthalate, a ketone such as acetone, benzonitrile, carbon bisulfide, dibutyl ether, and tetrachloroethane. A diester of phthalic acid is preferable from the standpoint of increasing the yield of the desired product.

After adding the FC reaction product to the solvent, the solvent in the FC reaction product system, such as an excess amount of a trihalide of phosphorus, is distilled off by vacuum distillation, the crystal grains of the complex are dissolved in the solvent, and the reaction system becomes entirely a liquid phase.

The solvent which is distilled off, such as a trihalide of phosphorus, can be reused as a raw material for the FC reaction.

Accordingly, in the present invention, most preferably, the FC reaction product system which is transformed into a substantially liquid state is reduced by yellow phosphorus in the presence of iodine. The typical reduction reaction which takes place is expressed by the following equation.

$$[\overset{+}{CH_3PCl_3}.\overset{-}{AlCl_4}] + (2/3)P \xrightarrow[\text{DEP}]{I_2} \quad (III)$$

$$CH_3PCl_2 + (2/3)PCl_3 + AlCl_3$$

There are no special restrictions on the conditions for the reduction reaction. The reaction can be carried out at room temperature or above and preferably between 40° C. and the boiling point of the system and under normal pressure for 1–3 hours while stirring is performed. After the reaction has been completed, aging can be performed for a short while.

In the present invention, if iodine is not added and only yellow phosphorus is employed, the reduction reaction progresses very little, and even if it progresses, the yield of the desired product is extremely low, so for practical purposes, it can be said that the reaction does not progress.

The discovery that the reduction reaction with yellow phosphorus in the presence of a catalyst in the form of iodine progresses rapidly was totally unexpected. The details of the reaction mechanism are still unclear, but it is thought that the reaction product of iodine and yellow phosphorus acts as a catalyst to promote the reduction reaction.

Iodine is effective even if added in a minute quantity. However, in many cases, the amount of iodine which is added is at most 10 weight % of the amount of yellow phosphorus which is employed and preferably is 2–5 weight %. The addition of more than 10 weight % is unnecessary and therefore uneconomical.

The amount of yellow phosphorus which is employed is generally 60–100 mole % and preferably 70–80 mole % with respect to the complex which is formed by the FC reaction.

After the completion of the reduction reaction, the desired alkyldihalogenophosphine is separated from the solvent and the aluminum chloride by a suitable means, and a high-purity alkyldihalogenophosphine is obtained with a high yield.

EXAMPLES

Next, the present invention will be described in further detail by means of the following examples.

EXAMPLE 1

133.34 g (1.0 mole) of anhydrous aluminum chloride and 824.10 g (6.0 moles) of phosphorus trichloride were charged into a 1-liter pressure-resistant glass reactor. The reactor was cooled while the mixture was stirred, and while maintaining the reaction temperature at 60° C., 26.76 g of methyl chloride were introduced over a period of 2 hours, and then another 26.76 g were gradually introduced over a period of 7 hours. Next, the temperature was gradually raised, and three hours later the reaction temperature reached 90° C. and the pressure reached 2.5 kg/cm². Heating was then continued for 5 hours in this state. When the reaction was completed, cooling was performed, upon which a crystallite complex thought to have the composition [CH$_3$PCl$_3$]+[AlCl$_4$]— separated out and the mixture became a slurry.

Next, 530 g of diethyl phthalate were charged into a 1-liter, 4-mouth flask equipped with a stirrer, a thermometer, a distilling apparatus, and a dropping funnel having a cooling jacket. The flask was then cooled, and the above-described FC reaction product was added to the flask at a room temperature. Distillation was then performed under a reduced pressure and phosphorus trichloride was recovered.

0.71 g of iodine were then added to the resulting liquid concentrate and the mixture was heated to 50° C. 20.00 g of liquid yellow phosphorus were then added by the dropping funnel over a period of two hours, after which aging by heating at the same temperature was performed for one hour. After the reaction was completed, vacuum distillation was performed while continuously adding 470 g of phosphorus trichloride into the liquid. 630g of distillate were obtained.

Quantitative analysis of the resulting distillate was performed by gas chromatography. The distillate was found to contain 16.74 weight % of methyl dichlorophosphine. Based on the initial amount of anhydrous aluminum chloride, the yield was 90.2%.

EXAMPLE 2

An FC reaction was performed in the same manner as in EXAMPLE 1

1 kg of dibutyl phthalate was charged into a 1.5-liter 4-mouth flask, and the FC reaction product obtained which was in the form of a slurry of a crystallite complex was added to the flask at room temperature. After phosphorus trichloride was distilled off by vacuum distillation, 0.71 g of iodine were added, the mixture was heated to 50° C., and 20.00 g of liquid yellow phosphorus were gradually added dropwise to the mixture. Then, after aging for one hour, vacuum distillation was performed while adding 470 g of phosphorus trichloride into the liquid. 590 g of distillate were obtained.

The resulting distillate contained 17.24 weight % of methyl dichlorophosphine. The yield based on anhydrous aluminum chloride was 87.0%.

EXAMPLE 3

A reaction similar to that of Example 2 was performed using 500 g of dimethyl phthalate instead of dibutyl phthalate.

628 g of distillate were obtained by vacuum distillation. The distillate contained 16.87 weight % of methyl dichlorophosphine. The yield based on anhydrous aluminum chloride was 90.6%.

EXAMPLE 4

133.34 g (1.0 mole) of anhydrous aluminum chloride and 824.10 g (6.0 moles) of phosphorus trichloride were charged into a 1-liter pressure-resistant glass reactor. While cooling the mixture to maintain a temperature of 60° C., 35.47 g of ethyl chloride were introduced over a period of 2 hours, and then a further 35.48 g were gradually introduced over a period of 6 hours. After the addition was completed, the temperature was gradually raised, and three hours later the reaction temperature reached 90° C. and the pressure reached 2.0 kg/cm². Reaction was then performed under these conditions for 5 hours.

Next, 530 g of diethyl phthalate were charged into a 1-liter, 4-mouth flask. The above-described FC reaction product was added to the flask at a temperature of at room temperature. After recovering phosphorus trichloride under reduced pressure, 0.71 g of iodine were added to the liquid concentrate. 19.20 g of liquid yellow phosphorus were added at 55° C. over a period of 3 hours under stirring and reduction was carried out. After the completion of the reaction, vacuum distillation was performed while continuously adding 470 g of phosphorus trichloride to the liquid. 642 g of distillate were obtained.

The resulting distillate contained 25.63 weight % of ethyl dichlorophosphine, and the yield based on anhydrous aluminum chloride was 92.0%.

COMPARATIVE EXAMPLE 1

The same FC reaction as for Example 1 was carried out, and a complex reaction product in the form of a diethyl phthalate solution was obtained. This reaction product was heated to 50° C. and 19.20 g of liquid yellow phosphorus were added over a period of 2 hours. However, the yellow phosphorus did not react but formed liquid grains. When 0.71 g of iodine were then added, the temperature of the liquid rose, the yellow phosphorus was gradually consumed, and the reaction progressed.

COMPARATIVE EXAMPLE 2

The same FC reaction as for Example 1 was carried out and an FC reaction product was obtained.

530 g of tetrachloroethane were charged into a 1-liter, 4-mouth flask, and the FC reaction product was added thereto. Phosphorus trichloride was then recovered by vacuum distillation. 19.20 g of liquid yellow phosphorus were then added at 100° C. over a period of 2 hours, after which reaction was carried out for 1 hour. After the completion of the reaction. Vacuum distillation was performed while adding 470 g of phosphorus trichloride to the liquid. 512 g of distillate were obtained.

The distillate contained 7.99 weight % of methyl dichlorophosphine. The yield based on anhydrous aluminum chloride was 35.0%.

EXAMPLE 5

An FC reaction was carried out in the same manner as in Example 1. After the completion of the reaction, phosphorus trichloride was distilled off using a rotary evaporator and a reaction product in the form of a complex was obtained.

530 g of carbon bisulfide were charged into a 1-liter, four-mouth flask, after which the complex which was formed by the FC reaction was introduced at room temperature and dissolved. Next, 0.71 g of iodine were added. 19.20 g of liquid yellow phosphorus were added dropwise at 40° C. over a period of two hours, and then reaction was performed for 1 hour at the same temperature. After the completion of the reaction, carbon bisulfide was distilled off, after which vacuum distillation was performed while adding 470 g of phosphorus trichloride to obtain 515 g of distillate.

The resulting distillate contained 18.5 weight % of methyl dichlorophosphine. The yield based on anhydrous aluminum chloride was 81.5%.

EXAMPLE 6

133.34 g of anhydrous aluminum chloride, 178.56 g of phosphorus trichloride, and 300 g of methylene chloride were charged into a 1-liter pressure-resistant glass reactor. The reactor was cooled while the mixture was stirred, and after the temperature reached 0° C. or below, the inside of the reactor was reduced to below atmospheric pressure using an aspirator. Next, 53.52 g of methyl chloride were introduced, and the temperature was gradually raised. After three hours, the temperature reached 80° C. and the pressure reached 3 kg/cm$^2$. Heating was then continued for 5 hours in this state. The reaction was then completed and cooling was performed, upon which a complex thought to have the composition $[CH_3PCl_3]+[AlCl_4]-$ separated out and the mixture became a slurry.

Next, 530 g of diethyl phthalate were charged into a 1-liter, 4-mouth flask equipped with a stirrer, a thermometer, a distilling apparatus, and a dropping funnel having a cooling jacket. The flask was then cooled, and the above-described FC reaction product was added at a temperature of at room temperature. Vacuum distillation was then performed, whereby methylene chloride and unreacted phosphorus trichloride were recovered.

0.71 g of iodine were then added to the resulting liquid concentrate and the mixture was heated to 50° C. 19.20 g of liquid yellow phosphorus were added by the dropping funnel over two hours, after which aging by heating at the same temperature was performed for one hour. After the reaction was completed, vacuum distillation was performed while continuously adding 480 g of phosphorus trichloride into the liquid. 630 g of distillate were obtained.

Quantitative analysis of the resulting distillate was performed by gas chromatography. The distillate was found to contain 15.09 weight % of methyl dichlorophosphine. Based on anhydrous aluminum chloride, the yield was 81.3%. A small quantity of small grains of red phosphorus was present in the distilling apparatus.

EXAMPLE 7

An FC reaction was carried out in the same manner as in Example 6, and a complex reaction product in the form of a diethyl phthalate solution was obtained.

Platinum-gold electrodes were set in a reduction reactor, and the oxidation-reduction potential was output to a recorder. After adding 0.71 g of iodine, the reaction mixture was heated to 50° C. and liquid yellow phosphorus was added in a dropwise manner. The electrical potential had been approximately 180 mV, but when the amount of yellow phosphorus being added reached 17.75 g, the electric potential suddenly fell to 165 mV, so at this point the dropwise addition was halted and aging by heating was carried out for one hour. Vacuum distillation was then performed while adding 480 g of phosphorus trichloride. 630 g of distillate were obtained.

The resulting distillate contained 15.27 weight % of methyl dichlorophosphine. The yield based on anhydrous aluminum chloride was 81.0%. The formation of red phosphorus in the distillation dregs was observed.

EXAMPLE 8

An FC reaction was carried out in the same manner as in Example 6. 1 kg of dibutyl phthalate was charged into a 1.5-liter four-mouth flask. At at temperature of at most 10° C., the complex in the form of a slurry which was obtained as the FC reaction product was added to the flask. Methylene chloride and unreacted phosphorus trichloride were distilled off by vacuum distillation, after which 0.71 g of iodine were added. While the oxidation-reduction potential was observed, the mixture was heated to 50° C. and liquid yellow phosphorus was gradually added in a dropwise manner. A change in electric potential was discerned when the amount of yellow phosphorus which had been added reached 17.50 g, so at that point the addition of yellow phosphorus was stopped. Aging was then performed for 1 hour, after which vacuum distillation was performed while adding 480 g of phosphorus trichloride to the liquid to obtain 580 g of distillate.

The resulting distillate contained 15.32 weight % of methyl dichlorophosphine. The yield based on anhydrous aluminum chloride was 76.0%.

EXAMPLE 9

The same procedure as in Example 8 was performed with the exception that 1 kg of benzonitrile was used instead of dibutyl phthalate.

572 g of distillate were obtained by vacuum distillation. The distillate contained 16.5 weight % of methyl dichlorophosphine. The yield based on anhydrous aluminum chloride was 80.6%.

EXAMPLE 10

133.34 g of anhydrous aluminum chloride, 178.56 g of phosphorus trichloride, and 300 g of methylene chloride were charged into a 1-liter pressure-resistant glass reactor. After the mixture was cooled, the inside of the reactor was reduced to below atmospheric pressure, and 70.95 g of ethyl chloride were added. The temperature of the mixture was gradually raised, and after 3 hours the reaction temperature reached 80° C. and the pressure reached 3 kg/cm$_2$, after which reaction was carried out for 5 hours.

530 g of diethyl phthalate were charged into a 1-liter, four-mouth flask, and at room temperature the FC reaction product was added thereto. Methylene chloride and unreacted phosphorus trichloride were recovered under reduced pressure, after which 0.71 g of iodine were added to the liquid concentrate. 19.20 g of liquid yellow phosphorus were added over a period of three hours at a temperature of 55° C. while the mixture was stirred, and reduction was carried out. After the completion of the reaction, vacuum distillation was performed while 480 g of phosphorus trichloride were continuously added to the liquid, and 642 g of distillate were obtained.

The resulting distillate contained 17.33 weight % of ethyl dichlorophosphine. The yield based on anhydrous aluminum chloride was 85.0%.

EXAMPLE 11

133.34 g of anhydrous aluminum chloride, 351.94 g of phosphorus trichloride, and 200 g of methylene chloride were charged into a 1-liter pressure-resistant glass reactor. After the mixture was cooled, the inside of the reactor was reduced to below atmospheric pressure and 104.5 g of methyl bromide were added. The temperature was then gradually increased, and after 3 hours the temperature reached 80° C. and the pressure reached 3 kg/cm$^2$. Reaction was then carried out under these conditions for 5 hours.

The complex which was formed as the FC reaction product was added to 530 g of diethyl phthalate at a temperature of at room temperature. Methylene chloride and unreacted phosphorus tribromide were recovered by vacuum distillation. 0.71 g of iodine were then added to the liquid concentrate, and at 50° C, 19.20 g of liquid yellow phosphorus were added in a dropwise manner. After the completion of the reaction, vacuum distillation was performed while adding 500 g of phosphorus tribromide to the liquid, and 620 g of distillate were obtained.

The resulting distillate contained 19.92 weight % of methyl dibromophosphine. The yield based on anhydrous aluminum chloride was 60.0%.

EXAMPLE 12

133.34 g of anhydrous aluminum chloride, 178.56 g of phosphorus trichloride, and 400 g of methylene chloride were charged into a 1-liter pressure-resistant glass reactor. While stirring the mixture, the reactor was cooled, and then the inside thereof was reduced to bllow atmospheric pressure. Next, the temperature was gradually increased, and after 3 hours the reaction temperature reached 100° C. and the pressure reached 5 kg/cm$^2$. Reaction was then carried out under these conditions for 5 hours.

530 g of diethyl phthalate were charged into a second 1-liter, 4 mouth reaction vessel. At a room temperature, the FC reaction product was added to the second reaction vessel. Methylene chloride was recovered from the mixture by vacuum distillation, upon which the reaction product was completely converted into a liquid phase system. Next, 0.71 g of iodine were added to the liquid, and at 50° C., 19.20 g of liquid yellow phosphorus were added to the liquid over a period of 2 hours, after which reaction was carried out for 1 hour. After the completion of the reaction, vacuum distillation was performed while continuously adding 480 g of phosphorus trichloride to the liquid. 580 g of distillate were obtained.

The resulting distillate contained 19.6 weight % of chloromethyl dichlorophosphine. The yield based on anhydrous aluminum chloride was 75.2%.

From the preceding description, it can be seen that the manufacturing method of the present invention uses an alkyl halide and a trihalide of phosphorus as starting materials, and the reaction product which is formed by an FC reaction is reduced by yellow phosphorus in the presence of iodine. As a result, an alkyldihalogenophosphine can be advantageously manufactured. In particular, by performing an FC reaction in the presence of an excess quantity of a trihalide of phosphorus, which can act as a solvent, and reducing the reaction product with yellow phosphorus in the presence of iodine, a high-purity alkyldihalogenophosphine can be easily manufactured with a high yield.

An alkyldihalogenophosphine manufactured by the method of the present invention is useful as an intermediate in the manufacture of pesticides, flame retardants, and other organic phosphides. Therefore, the fact that alkyldihalogenophosphine can be manufactured with high yield gives the present method great industrial value in the manufacture of pesticides and other products.

In addition, the method of the present invention is simpler than manufacturing methods using direct reaction of methane and a halide of phosphorus. Furthermore, it does not require excess investment in equipment for performing separation or ensuring safety, making it even more advantageous from an industrial standpoint.

What is claimed is:

1. A manufacturing method for an alkyldihalogenophosphine, comprising reducing the reaction product of a Friedel-Crafts reaction between an alkyl halide and a trihalide of phosphorus using yellow phosphorus in the presence of iodine as a catalyst.

2. A manufacturing method as claimed in claim 1, wherein said Friedel-Crafts reaction is carried out using an excess amount of a trihalide of phosphorus which can act as a reaction solvent.

3. A manufacturing method as claimed in claim 1, wherein said Friedel-Crafts reaction is carried out using methylene chloride as a solvent.

4. A manufacturing method as claimed in claim 1, wherein said reaction product of said Friedel-Crafts reaction is crystallized to form crystallite grains by the addition of an alkyl halide in a controlled manner.

5. A manufacturing method as claimed in claim 1, wherein said alkyl halide is methyl chloride or ethyl chloride.

6. A manufacturing method as claimed in claim 5, wherein the amount of iodine which is used as a catalyst is at most 10 weight % with respect to the yellow phosphorus.

7. A manufacturing method as claimed in claim 1, wherein said reaction product is added to a polar solvent having affinity for anhydrous aluminum chloride, said trihalide of phosphorus is then separated by vacuum distillation, and the reaction product is then reduced.

8. A manufacturing method as claimed in any one of claims 1-5, wherein vacuum distillation of the reaction product which was reduced by yellow phosphorus is performed while a trihalide of phosphorus is added thereto and said alkyldihalogenophosphine is recovered.

* * * * *